Figure 1:
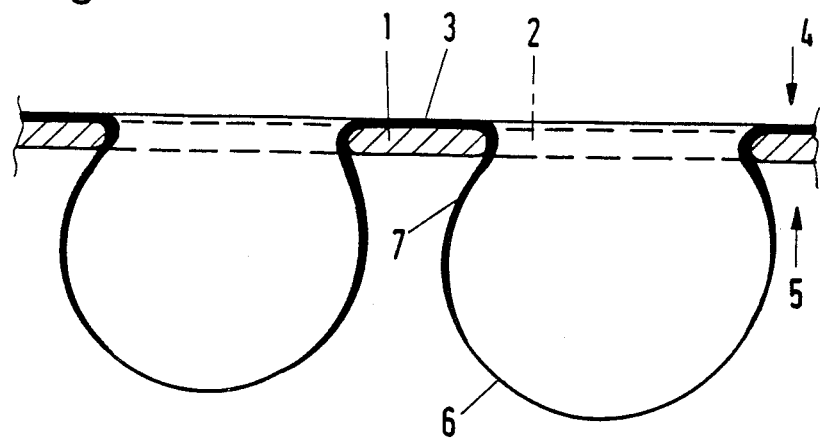

United States Patent [19]

Rose

[11] Patent Number: 4,895,749
[45] Date of Patent: Jan. 23, 1990

[54] LIQUID PERMEABLE THERMOPLASTIC FILMS

[75] Inventor: Dieter Rose, Grunwald, Fed. Rep. of Germany

[73] Assignee: AOE Plastic GmbH, Fed. Rep. of Germany

[21] Appl. No.: 215,732

[22] Filed: Jul. 6, 1988

[30] Foreign Application Priority Data

Jul. 15, 1987 [DE] Fed. Rep. of Germany ....... 3723404

[51] Int. Cl.$^4$ ............................................... B32B 3/10
[52] U.S. Cl. ..................................... 428/132; 428/178; 428/192; 264/504; 264/544; 264/553; 264/554
[58] Field of Search .................. 428/132, 128, 192; 264/554, 504, 553, 544

[56] References Cited

U.S. PATENT DOCUMENTS

| | | | |
|---|---|---|---|
| 2,234,842 | 3/1941 | Jordan | 264/504 |
| 3,929,135 | 12/1975 | Thompson | 128/287 |
| 4,276,336 | 6/1981 | Sabee | 428/132 |
| 4,552,709 | 11/1985 | Koger et al. | 264/504 |

FOREIGN PATENT DOCUMENTS

| | | |
|---|---|---|
| 0057484 | 1/1982 | European Pat. Off. . |
| 0156471 | 10/1985 | European Pat. Off. . |
| 0203823 | 12/1986 | European Pat. Off. . |
| 0205286 | 12/1986 | European Pat. Off. . |
| 0233673 | 8/1987 | European Pat. Off. . |
| 2556501 | 7/1976 | Fed. Rep. of Germany . |
| 030524 | 9/1977 | Japan . |
| 2014508A | 8/1979 | United Kingdom . |

Primary Examiner—Ellis P. Robinson
Assistant Examiner—P. J. Ryan
Attorney, Agent, or Firm—Brooks Haidt Haffner & Delahunty

[57] ABSTRACT

Thermoplastic film, permeable to liquids, used particularly as a covering film for absorbent material, whose openings are formed as projections on one side only of the film, and having its narrowest cross-section in a plane different from that of the smooth side of the film. The cross-section of the opening widens on passing from its narrowest point towards the free edge of the projection on film. The free edge of the projection can be irregularly lobed or wrinkled.

7 Claims, 1 Drawing Sheet

LIQUID PERMEABLE THERMOPLASTIC FILMS

The invention concerns a liquid-permeable thermoplastic film having openings shaped as projections terminating in a free edge on one side only of the film, the narrowest cross-section of the projection being on a different plane from that of the opposite smooth side of the film.

The liquid permeable film of the present invention is intended mainly as a covering film for absorbent material, particularly for sanitary towels and similar articles of hygiene such as plasters, mattress pads or baby napkins. In these applications, the smooth side of the film forms the external surface of the package in which the absorbent material is wrapped, while the other side of the film with the projections is in contact with the absorbent material.

Conventional films which are permeable to liquids and are used as covering films for baby napkins (DE-PS 25 56 501) have embossed elements forming the openings on one side of the film, these elements tapering, in the form of a truncated cone, towards the opening on that side of the film. The smallest cross-section of these embossed elements is therefore at the free end of the opening, on the side of the film with the embossed elements. As a result, backflow of the liquid itself is effectively prevented when pressure is exerted on the napkin. This effect is due to the fact that the openings in the embossed elements are constricted when pressure is exerted in the direction of their longitudinal axis so that they behave like a non-return valve. A pre-condition for achieving this effect is that the narrowest cross-section of the openings of the embossed elements are as small as possible in relation to the width of the openings on the opposite smooth side of the film. This, however, has the disadvantage that the permeability of liquids of viscosity higher than that of water is too low for many applications, e.g. for sanitary towels where it is desirable to have larger individual openings without however impairing their capillary absorption capacity, although this capillary action naturally decreases with increasing opening diameter.

The purpose of the invention is therefore to provide a perforated film which has a good permeability, even for liquids of significantly higher viscosity than e.g. water.

In the present invention the problem is solved by increasing the cross-section of the openings from the point on the film where it is at its narrowest towards the free edge of the projections on the film.

According to the present invention is a liquid-permeable film made from a thermoplastic material suitable for use as a covering film for absorbent material having openings therein shaped as projections which terminate in a free edge on one side only of the film, the narrowest cross-section of the opening being on a different plane from that of the opposite smooth side of the film, and characterised by the fact that the cross-section of the opening increases in size in an axial direction from the point of the narrowest cross section (1) to the free edge of the projections (12).

It has now been found that in this way a surprisingly good absorption is achieved despite the reduced capillary effect of the larger diameters of such openings. It was shown, for example, that sanitary towels provided with a covering of a film in accordance with the invention are significantly more absorbent than those provided with a covering of films previously used or even in those cases in which the covering film is in the form of netting.

The cross-section of the opening in the axial direction of the projections away from its narrowest cross-section is at least as large as that of the opening in the film on the opposite smooth side.

The circumferential length of the free edge of the projections on average, is suitably at least about 10%, preferably more than 20%, greater than that of its cross-section at the narrowest point. It was found that the capillary effect of the openings is improved if the free edge of the opening of the projection is of an irregularly lobed and/or wrinkled form. This can be further improved if the thickness of the film in the region of the free edge of the projection is substantially thinner than the undeformed film, the latter preferably being several times thicker than the free edge of the opening.

By ensuring the above, it was found that the projections can bridge in concertina-fashion the fluctuating distances between the film and the absorbent material. If the distance is large or the pressure low, they adjust, due to the inherent elasticity of the material, to their maximum relaxes length, and thus achieve a relatively high probability of contact with the absorbent material; under pressure, they can squeeze together, concertina-fashion, without thereby reducing the cross-section of the openings and impairing the absorption capacity.

It is advisable to ensure that the mean distance between the plane of the smooth side (i.e. the plane of the undeformed film surface) and the plane containing the narrowest cross-section of the openings is greater than three times the thickness of the undeformed film in its relaxed state.

According to a further embodiment the present invention is a method for the production of a perforated thermoplastic film, in which the film, in its hot plastic state, lying on a perforated plate, is forced, by differential pressure, into the perforations in the plate, and allowed to burst inside, characterised by the fact that the thickness of the plate (1) and the deformation properties of the film (3) are such that, under the effect of the differential pressure before bursting behind the perforations (2) in the plate (1), bubbles (6) are formed, of a diameter exceeding the average diameter of the perforations (2).

In the production of conventional perforated film, the thermoplastic film in its hot plastic state, lying on a perforated plate, is sucked into the perforations in the plate by differential pressure and is allowed to burst inside them, the shape of the perforations on the plate corresponding to the required shape of the projections. According to the invention, this process is modified so that the plates used are very thin in relation to the diameter of its perforations, and the material characteristics at the deformation temperature are such that before the film drawn into the perforations bursts, bubbles, whose diameter is larger than that of the perforations on the plate, are formed on the side of the plate away from that on which the thermoplastic film is lying. The required lobe-shaped or irregular or wrinkled structure of the free edges of the projections is thereby achieved automatically.

In contrast to those perforated plates that are used in the conventional production methods and in which the shape and size of the perforations correspond to the shape and size of the required projections, in the method relating to the invention, a significant proportion of the projections is formed on the side opposite to that on which the thermoplastic film is lying. The shape of the perforations on the plate is not critical in the present invention. The thickness of the perforated plate is preferably not more than the smallest diameter of the perforation and, better still, less than one third of the smallest diameter of the perforations.

Figure 2:
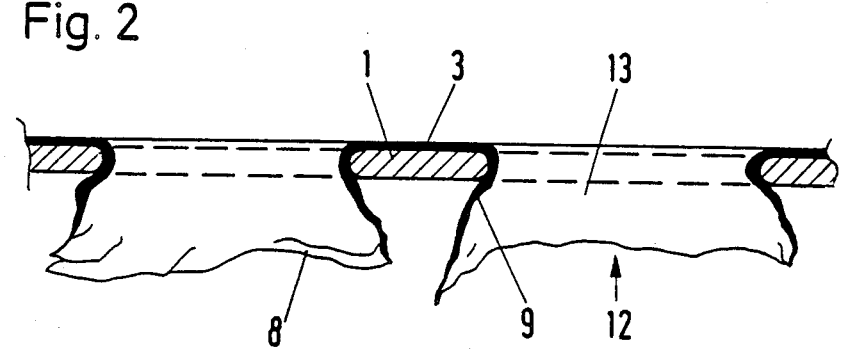

The invention is explained below in more detail by reference to the drawings which illustrate the following:

FIGS. 1 and 2: two states during the production process, and

Figure 3:
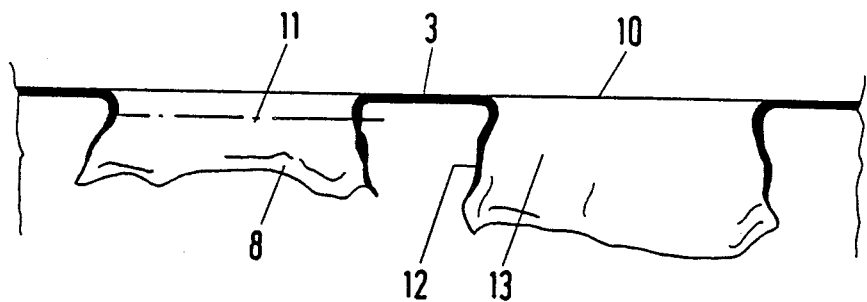

FIG. 3: the finished film, illustrating the enlarged cross-section of the projections in each case.

A hot thermoplastic plastic film 3, whose initial thickness is preferably between 0.015 and 0.07 mm, is laid on a perforated metal plate 1 whose thickness is of the order of 0.2 mm and whose uniformly distributed perforations 2 have an average diameter of the order of 0.8 mm. By means of a differential pressure that act from the smooth side 4 of the film to the projection side 5 of the film, the film is blown through the perforations 2 into bubbles 6 whose average diameter is greater than that of the perforations 2, so that the film in the region 7 is deformed laterally, at a point beyond the extremities of each perforation. Due to the degree of deformation, which exceeds the degree of elasticity, and due to the cooling to which the hot film is subjected after deformation, particularly in the contact area and in the vicinity of the perforated metal plate 1, shape recovery occurs only to a limited extent. In the region 7, the average diameter of the bubble, which is greater than the average diameter of the perforation, is largely maintained, while the material fraction that previously formed the bubble connection is largely withdrawn to this region 7. Since bursting of the bubble does not take place in a geometrically uniform manner, the free edge 8 is formed having the already mentioned lobe-like, undulating, non-uniform, fissured and/or wrinkled structure.

During the subsequent course of the process, the deformed material 3 is removed from the perforated plate 1, the projections 9 thus formed being withdrawn through the perforations 2 in the plate 1. The projections which are now on one side only of the film, retain the widened edge shape shown in FIG. 3, this shape being at least partly responsible for the good capillary behaviour of the film according to the invention together with the special structure of the free edge of the projections. The irregularity of the free edge of the projection can be increased or reduced as desired by controlling the production process and by choosing the thermoplastic material with appropriate characteristics. The shape of the openings is characterised by the fact that their cross-section in the plane 10 on the smooth side decreases in the direction of plane 11 with the narrowest cross-section, and increases again as one progresses further in the longitudinal direction of the projection.

The smallest diameter ie the narrowest cross-section of the opening on the film is suitably from 0.2 to 2 mm, preferably 0.3 to 1.2 mm.

The depth of the projections can be selected depending on the application. It is suitably from 0.2 to 2 times the smallest opening diameter ie the narrowest cross-section of the opening.

The film is extremely compatible with human skin because on the one hand the degree of covering is slight, due to the large area occupied by the openings in the relation to the total area, and on the other hand the material is soft but has a high tensile strength. The softness is due to the flexibility of the thinned free edges of the projections. The good strength values are due to the fact that the regions with the smallest diameter of the projections in which the greatest stresses occur when the film is subjected to tensile stress do not simultaneously form the free edge of the opening and are therefore not impaired by notch effects or portions where the film is considerably thinner.

Polyolefins, including their homopolymers, mixtures of homopolymers, copolymers, mixtures of various copolymers, and mixtures of copolymers and homopolymers, are preferred as thermoplastic film forming material.

It is not necessary for the shape of the openings in the film and perforations on the metal plate to be circular; it may also be polygonal or oblong or slightly elongated. With a polygonal design, the diameter details given above must be related to the mean diameter, and with an elongated version, to the transverse dimension.

I claim:

1. Liquid-permeable film made from a thermoplastic material suitable for use as a covering film for absorbent material having openings therein shaped as projections which terminate in a free edge on one side only of the film, the narrowest cross-section of the opening being on a different plane from that of the opposite smooth side of the film, and characterised by the fact that the plane of the narrowest cross-section of the opening is spaced from the plane of said opposite smooth side of the film in the direction from said opposite smooth side toward said one side of said film by a distance greater than the thickness of said film in its undeformed state and that the cross-section of the opening increases in size in an axial direction from the point of the narrowest cross-section (11) to the free edge of the projection (12).

2. A film, according to claim 1, characterised by the fact that the cross section of the openings (13) in the axial direction of the projection (12) away from its narrowest cross-section is at least as large as that of the opening in the film on the opposite smooth side.

3. A film, according to claim 1, characterised by the fact that the circumferential length of the free edge (8) of the projections (12) is, on average, about 10% greater than that of its cross-section at the narrowest point.

4. A film, according to claim 1, characterised by an irregularly lapped and/or folded shape of the free edge (8) of the projections (12).

5. A film, according to claim 1, characterised by the fact that the thickness of the film in the region of the free edge (8) of the projection (12) is several times less than the thickness of the undeformed film.

6. A film, according to claim 1, characterised by the fact that the average thickness of the film from the plane (10) of the film on the smooth side to the plane (11) of the film with the narrowest cross-section of the openings (13), of the film, is greater than three times the thickness of the undeformed film in its relaxed state.

7. A method for the production of a perforated thermoplastic film, according to claim 1, in which the film, in its hot plastic state, lying on a perforated plate, is forced, by differential pressure, into the perforations in the plate, and allowed to burst inside, characterised by the fact that the thickness of the plate (1) is small relative to the average diameter of said perforations (2) and the deformation properties of the film (3) are such that, under the effect of the differential pressure before bursting behind the perforations (2) in the plate (1), bubbles (6) are formed, of a diameter exceeding the average diameter of the perforations (2).

* * * * *

UNITED STATES PATENT AND TRADEMARK OFFICE
CERTIFICATE OF CORRECTION

PATENT NO. : 4,895,749
DATED : January 23, 1990
INVENTOR(S) : DIETER ROSE

It is certified that error appears in the above-identified patent and that said Letters Patent is hereby corrected as shown below:

Col. 3, l. 19, add an "s" to the word --act--.

Col. 3, l. 40, should read "deformed film 3"

Col. 3, l. 66-67, should read "in relation to the"

Col. 4, l. 15, add an "s" to the word "film"

Signed and Sealed this

Fifth Day of March, 1991

Attest:

HARRY F. MANBECK, JR.

*Attesting Officer*  *Commissioner of Patents and Trademarks*